United States Patent
Dao et al.

(10) Patent No.: US 11,214,917 B2
(45) Date of Patent: Jan. 4, 2022

(54) OXIDIZED CELLULOSE-BASED MATERIAL, METHOD FOR OBTAINING SAME AND USE THEREOF AS COMPRESS

(71) Applicant: SYMATESE, Chaponost (FR)

(72) Inventors: Vithuy Dao, Fresnes (FR); Robert Michelot, Antony (FR); Benjamin Herbage, La Mulatiere (FR); Fabien Fuchez, Montrottier (FR); Eric Perouse, Paris (FR)

(73) Assignee: SYMATESE, Chaponost (FR)

( * ) Notice: Subject to any disclaimer, the term of this patent is extended or adjusted under 35 U.S.C. 154(b) by 0 days.

(21) Appl. No.: 16/507,768

(22) Filed: Jul. 10, 2019

(65) Prior Publication Data

US 2019/0330794 A1  Oct. 31, 2019

Related U.S. Application Data

(62) Division of application No. 14/404,842, filed as application No. PCT/FR2013/051255 on Jun. 3, 2013, now abandoned.

(30) Foreign Application Priority Data

Jun. 4, 2012 (FR) ...................... 1255182

(51) Int. Cl.
| | | |
|---|---|---|
| *C08B 15/04* | (2006.01) | |
| *D06M 11/30* | (2006.01) | |
| *A61L 15/28* | (2006.01) | |
| *D06M 13/355* | (2006.01) | |
| *D06M 13/388* | (2006.01) | |
| *D06M 11/64* | (2006.01) | |
| *A61L 15/64* | (2006.01) | |
| *D06M 101/06* | (2006.01) | |

(52) U.S. Cl.
CPC ............ *D06M 11/30* (2013.01); *A61L 15/28* (2013.01); *A61L 15/64* (2013.01); *C08B 15/04* (2013.01); *D06M 11/64* (2013.01); *D06M 13/355* (2013.01); *D06M 13/388* (2013.01); *D06M 2101/06* (2013.01); *D10B 2201/20* (2013.01); *Y02P 20/582* (2015.11); *Y10T 428/249921* (2015.04)

(58) Field of Classification Search
CPC ................ C08B 15/04; C08B 15/02
See application file for complete search history.

(56) References Cited

U.S. PATENT DOCUMENTS

| 4,543,410 A | 9/1985 | Cruz, Jr. |
| 6,716,976 B1 | 4/2004 | Jetten et al. |
| 2015/0147558 A1 | 5/2015 | Dao et al. |

FOREIGN PATENT DOCUMENTS

| EP | 0492990 A1 | 7/1992 | |
| EP | 1215217 A1 | 6/2002 | |
| EP | 1462123 A1 | 9/2004 | |
| EP | 2216345 A1 | 8/2010 | |
| EP | 2279762 A1 | 2/2011 | |
| WO | 0050462 A1 | 8/2000 | |
| WO | 0134656 A1 | 5/2001 | |
| WO | WO-0134656 A1 * | 5/2001 | ............ D21H 11/20 |
| WO | 2009016325 A2 | 2/2009 | |
| WO | 2012119229 A1 | 9/2012 | |

OTHER PUBLICATIONS

International Search Report for PCT/FR2013/051255 dated Sep. 25, 2013.
Fujisawa, et al; "Preparation and characterization of TEMPO-oxidized cellulose nanofibril films with free carboxyl groups," Carbohydrate Polymers, Feb. 11, 2011, pp. 579-583, vol. 84, issue 1, abstract only.
Kumar, et al; "Analysis of carboxyl content in oxidized celluloses by solid-state 130 CP/MAS NMR spectroscopy," Int J Pharm, Jul. 20, 1999, pp. 219-226, vol. 184, issue 2, abstract only.
Singh, et al; "Potential biosoluble carriers: biocompatibility and biodegradability of oxidized cellulose," Biomater Med Devices Artif Organs, 1979, pp. 495-512, vol. 7, issue 4, abstract only.

* cited by examiner

*Primary Examiner* — Shaojia A Jiang
*Assistant Examiner* — Everett White
(74) *Attorney, Agent, or Firm* — Heslin Rothenberg Farley & Mesiti P.C.

(57) ABSTRACT

The present invention relates to a method of obtaining a solid material based on a polymer having its cellobiose units exhibiting the following characteristics:
  at least some of the cellobiose units have at least one carboxylic acid function attached to the $C_6$ carbon, the other $C_6$ carbons having a primary alcohol function attached thereto; and
  at least some of the cellobiose units have at least one of the two rings open between the $C_2$ and $C_3$ carbons, the other $C_2$ and $C_3$ carbons forming a ring and having an alcohol function attached thereto. Such a material, advantageously a textile, may be used as a compress.

21 Claims, No Drawings

OXIDIZED CELLULOSE-BASED MATERIAL, METHOD FOR OBTAINING SAME AND USE THEREOF AS COMPRESS

CROSS-REFERENCE TO RELATED APPLICATIONS

This application is a divisional application of U.S. patent application Ser. No. 14/404,842, filed with the U.S. Patent and Trademark Office on Dec. 1, 2014, which is a National Stage Entry under Section 371 of International Application No. PCT/FR2013/051255, filed on Jun. 3, 2013, which claims priority to French Application No. 1255182 (filed on Jun. 4, 2012). The entire contents of each of the prior applications are hereby incorporated herein by reference.

FIELD OF THE INVENTION

The present invention provides a novel solid material based on polymer containing at least partially oxidized cellobiose units, capable of being used in the medical field, particularly as a compress.

Such a material, advantageously a textile, may be obtained by submitting a solid material based on a polymer containing cellobiose units to a method in at least two steps: placing it in contact with an oxidizing mixture comprising a hypohalite, a halite, and an oxo-ammonium salt or a precursor of said salt; placing in contact the material thus processed with a solution of periodic acid or of a salt thereof; and then, possibly, placing in contact the material thus processed with a halite.

STATE OF THE ART

Surgical haemostatic compresses, or compresses, should be haemostatic, absorbable, and easy to manipulate by surgeons. Such properties may be obtained due to textiles based on oxidized cellulose.

As a reminder, cellulose is a homopolymer belonging to the class of polysaccharides. It is formed of a linear chain of glucose molecules or anhydroglucose units (D-anhydroglucopyranose), interconnected by glycosidic bonds β-1,4. Cellulose may also be defined as a chain of cellobiose units:

Currently, such compresses are obtained by submitting the cellulose-based textile to the action of $NO_2$ in the presence of solvents, such as described, for example, in document EP 0492990. Thus, the reference product, currently commercialized under trade name Surgicel®, is obtained by means of such a method.

However, such a technology requires expensive, dangerous raw materials, which are difficult to recycle, as well as a demanding installation. This is why other ways have been attempted to be developed to obtain compresses.

Document WO 2009/016325 describes an alternative method of oxidizing cellulose within a fabric, by means of an oxidizing catalytic system comprising 1-oxo-2,2,6,6-tetramethylpiperidine-1-oxide (TEMPO), NaBr, and NaClO. This reaction occurs at low temperature and at a basic pH which has to be strictly controlled during the reaction.

In parallel, it is for example known from document EP 2216345 that the oxidizing of cellulose by an oxidizing system comprising TEMPO, NaClO, and $NaClO_2$ results in cellulose partially oxidized selectively at the level of the primary alcohol at $C_6$, having a high degree of polymerization, a good mechanical resistance and a good lightfastness.

Further, Singh et al. have described a cellulose oxidation method, based on the use of sodium periodate. The cellulose thus processed, which exhibits aldehyde functions and a ring opening, has a slow in vivo absorption. The aldehyde functions may be used to immobilize, in particular, enzymes of interest.

There however is an obvious need to develop novel oxidized cellulose compresses. Properties desired for such compresses are, in particular:
- satisfactory haemostatic properties;
- a controllable absorption, advantageously in the order of 2 weeks after implantation in the organism;
- a good mechanical stability;
- the ability to be obtained by means of a low-cost method and easily transposable at an industrial level.

DISCUSSION OF THE INVENTION

The present invention provides a novel solid material based on oxidized cellulose, usable as a compress and capable of being obtained due to an original process.

Thus, and according to a first aspect, the present invention provides a solid material based on a polymer containing cellobiose units, wherein:
- at least some of the cellobiose units have at least one of the two primary alcohol functions, attached to the $C_6$ carbon, oxidized into a carboxylic acid function;
- at least some of the cellobiose units have at least one of the two rings open between the $C_2$ and $C_3$ carbons.

In the context of the present invention, "solid material" means fibers or microfibrils, as well as assemblies of fibers or fibers assembled in the form of a yarn, or in the form of a fabric made of yarns, weaved or knitted, for example, or

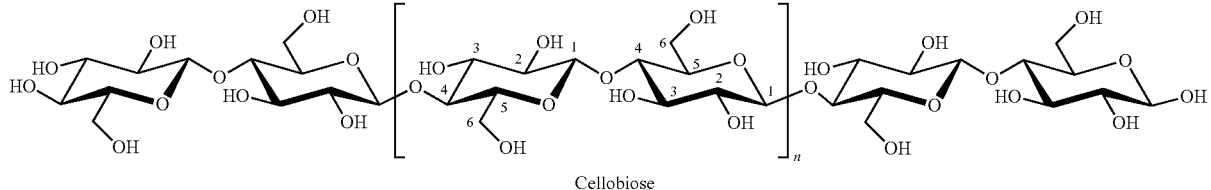

Cellobiose also in the form of a nonwoven, or also in the form of a sheet of fibers forming an oriented matrix, or also in foam or powder form.

In the context of the present invention, "yarn" designates a linear assembly of interconnected fibers (or of microfilaments). A cellulose yarn thus should be distinguished from a cellulose fiber, which designates an individual object, and not an assembly of objects. According to a specific embodiment, the solid material does not correspond to individualized fibers. Typically, a yarn is obtained by spinning of fibers of the same type, but may also be obtained by spinning of different fibers, such as for example, cellulose fibers in combination with synthetic fibers.

In a preferred embodiment, the yarns are knit in a fabric. Different stitches can be envisaged, particularly jersey (conventionally knit with a 42-filament 220-dtex yarn) or crochet (advantageously knit with 40-filament 110-dtex yarn).

Preferably, the solid material is a textile. In the context of the invention, "textile" means an assembly of yarns or of fibers, advantageously attached together, forming a strong and insoluble entity. Thus, and in appropriate fashion, the textile may be a fabric, advantageously obtained by weaving or knitting of yarns, or a non-woven obtained by assembly of fibers.

The polymer forming the fibers of the material according to the invention contains cellobiose units. It may for example be natural cellulose or modified cellulose.

In the case of modified cellulose, it advantageously is viscose, which corresponds to regenerated cellulose.

The fibers used according to the invention are for example obtained from natural cellulose, that is, fibers directly originating from a plant, either by being harvested on the plant, or by being obtained by a mechanical processing of the plant, such as by a milling, pressing, crushing, and/or separation. The cellulose fibers also are modified cellulose fibers, that is, natural cellulose or solubilized natural cellulose, having reacted with a chemical component.

Term "cellulose fibers" also includes, in the sense of the present invention, regenerated cellulose fibers, that is, fibers of natural cellulose, possibly modified, solubilized in a solvent, and then shaped back in the form of fibers.

Example of natural cellulose fibers originating from plants are cotton, hemp, jute, or wood pulp. Such cellulose fibers may also be of bacterial origin.

Artificial cellulose fibers are obtained by a natural cellulose processing process.

Expression "based on a polymer containing cellobiose units" means that this polymer forms the main, if not the single, ingredient of the material. It is however not excluded for the material to contain other components, for example at least another polymer containing no cellobiose units such as polymers forming synthetic fibers. In a specific embodiment, other polymers possibly containing anhydroglucose units may be associated, such as alginate, hyaluronic acid, starch, or other glycosaminoglycans.

"Polymer containing cellobiose units" designates a polymer which comprises at least two cellobiose units in its chain, and in a limiting case which is only formed of cellobiose units, such as cellulose.

According to the invention, said polymer is modified, at least partially, at the level of its cellobiose units.

According to a first preferred characteristic of the polymer, at least some of the cellobiose units have at least one of the two primary alcohol functions, attached to the $C_6$ carbon, oxidized into a carboxylic acid function. In other words, the function attached to the $C_6$ carbon is either an alcohol function, or a carboxylic acid function. The presence of an aldehyde function at the $C_6$ level is thus advantageously excluded.

At the level of a cellobiose unit of the polymer, several cases may occur:
- the two anhydroglucose units forming the cellobiose unit exhibit a (non modified) primary alcohol function at $C_6$;
- the two anhydroglucose units forming the cellobiose unit exhibit a carboxylic acid function at $C_6$;
- one of the two anhydroglucose units forming the cellobiose unit exhibits a carboxylic acid function at $C_6$, the other exhibiting an alcohol function at $C_6$.

According to a second preferred characteristic of the polymer, at least some of the cellobiose units have at least one of the two rings open between $C_2$ and $C_3$. In other words, the $C_2$ and $C_3$ carbons may be unmodified, that is, they form a ring and have an alcohol function attached thereto. Thus, the presence of a ketone function at the $C_2$ and/or $C_3$ level is advantageously excluded. As a variation, the ring between the $C_2$ and $C_3$ carbons may be open. In this case, and advantageously, the $C_2$ and/or $C_3$ carbons may have aldehyde and/or carboxylic functions, possibly functionalized, attached thereto. Acetal and semi-acetal functions, resulting from the reaction of alcohol groups with aldehyde groups, may also be present.

Again, at the level of a cellobiose unit of the polymer, several cases may occur:
- the two anhydroglucose units exhibit $C_2$ and $C_3$ carbons engaged in the ring and having an alcohol function (non modified) attached thereto;
- the two anhydroglucose units have an open ring between carbons $C_2$ and $C_3$, the latter advantageously bearing aldehyde and/or carboxylic acid functions, possibly functionalized;
- one of the two anhydroglucose units forming the cellobiose unit has an open ring between carbons $C_2$ and $C_3$, the latter advantageously having aldehyde and/or carboxylic acid functions, possibly functionalized, attached thereto; the other anhydroglucose unit is non modified, that is, carbons $C_2$ and $C_3$ are engaged in the ring and have an alcohol function attached thereto.

According to the invention, these two characteristics should be present in the polymer, at the level of at least one cellobiose unit or possibly at the level of at least two different cellobiose units, each having one of the two above-described characteristics.

In the case where the polymer containing cellobiose units is cellulose or viscose, the polymer forming the material according to the invention thus is a derivative of cellulose or of viscose, more precisely an oxidized derivative.

According to a preferred embodiment and as will be described hereafter, the first characteristic can be given to the material by submitting it to the action of an oxidizing mixture comprising a hypohalite, a halite, and an oxoammonium salt or a precursor of said salt. However, any method of converting the primary alcohol group attached to the $C_6$ carbon exclusively into a carboxylic acid group is a possible alternative to the use of the above-described oxidizing mixture. Thus, other methods enabling to selectively oxidize the $C_6$ carbon of an anhydroglucose unit may be implemented, particularly by means of nitrosonium ions (essentially TEMPO and derivatives), with or without catalysis by transition elements, with or without NaBr, with or without oxidizing enzyme, with or without complexing agent, such as for example described in U.S. Pat. No. 6,716,976.

Thus, and at this stage, at least a portion of, and possibly all the anhydroglucose units of the polymer are converted into glucuronic units. The polymer present thus corresponds to a polyglucuronic acid.

Without relating to any theory, this first step would enable to control the acidity of the fabric, which is an important property for haemostasis. However, at the end of this step, the obtained material is poorly absorbable, which property is improved due to the implementation of the second step of the method according to the invention:

According to a preferred embodiment and as will be described hereafter, the opening of the ring between the $C_2$ and $C_3$ carbons is obtained by submitting the material to the action of a solution of periodic acid or of a salt thereof. Here again, any alternative method enabling to open the ring between $C_2$ and $C_3$ and to oxidize the alcohol functions attached to these carbons may be implemented.

In known fashion, the periodate treatment causes, in addition to the opening of the ring between the $C_2$ and $C_3$ carbons, the oxidation of the alcohol functions attached to these carbons into aldehyde functions. Such functions may be used for the grafting of molecules of interest, such as enzymes, thus enabling to functionalize the material.

Further, the aldehyde functions may be converted into carboxylic acid functions. The carboxylic acid functions may also be functionalized, to generate, for example, ester or amide functions.

Thus, the material according to the invention is rich in carboxylic acid functions which may be attached to:
- the $C_6$ carbon;
- the $C_6$ carbon and the $C_2$ carbon;
- the $C_6$ carbon and the $C_3$ carbon;
- the $C_6$ carbon, the $C_2$ carbon, and the $C_3$ carbon.

It should be noted that in the context of the invention, the carboxylic acid functions may be in protonated form or in the form of carboxylate ions, for example, complexed with calcium.

Advantageously, the general oxidation degree or rate of the material according to the invention, which corresponds to the conversion of the alcohol and/or aldehyde functions into carboxylic acid functions, is greater than 10%, advantageously greater than 12%, or even greater than 15%.

As a reminder, the oxidation degree or rate is defined as the mass of the carboxylic acid groups contained in 100 g of the material. The measurement of the oxidation of the polymer, particularly of the cellulose, may be for example evaluated by titrimetry, according to the protocol described by Sobue and Okubo by using the methodology described in the US pharmacopeia, by nuclear magnetic resonance (NMR) (Kumar et al.), or also by infrared spectrometry (Fujisawa et al).

As a reminder and according to the invention, the polymer should have the two previously-mentioned characteristics. In practice, the polymer chain should have:
- cellobiose units having only one or the two primary alcohol functions, attached to the $C_6$ carbon, oxidized into a carboxylic acid function. The possible $C_6$ carbon having no carboxylic acid function attached thereto bears a primary alcohol function. Further, the cellobiose units remain non modified at the level of the $C_2$ and $C_3$ carbons that is, they are engaged in the ring and have an alcohol function attached thereto;
- cellobiose units only having one or the two rings open between the $C_2$ and $C_3$ carbons. The possible non-open ring between $C_2$ and $C_3$ has alcohol functions attached to the $C_2$ and $C_3$ carbons. Further, these cellobiose units remain non-modified at the level of the $C_6$ carbon, that is, the latter has a primary alcohol function attached thereto;
- cellobiose units having both at least one of the two primary alcohol functions attached to the $C_6$ carbon, or even both, oxidized into a carboxylic acid function and at least one of the two rings open between carbons $C_2$ and $C_3$, or even both, as illustrated in the following diagram for a cellobiose anhydroglucose where the $C_2$ and $C_3$ carbons have aldehyde functions attached thereto:

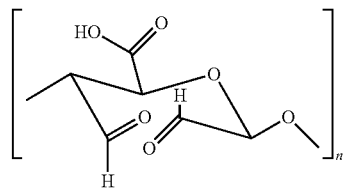

In the context of the present invention, it has been demonstrated that a solid material, particularly in textile form and having the above-discussed structural characteristics, can be used as a medical compress, capable of having the expected properties in terms of mechanical stability, or aging strength, of haemostatic properties, and or absorbability.

In the context of the invention, "mechanical stability" designates the fact that the material can be handled with tools, particularly pliers, or even manually, while keeping a good mechanical behavior. The mechanical stability also gives the material the property of being capable of being kept in store for several months, or even several years, at ambient temperature, without for its integrity to be altered.

In the context of the invention, "haemostatic" means the fact that the material is capable of stopping bleeding when it is locally applied.

In the context of the invention, "absorbable character" means the fact that the material is totally or mainly degraded in vivo 2 weeks after implantation, advantageously after 1 week.

The absorption may be quantified visually, by observing the degree of degradation of the material, or by any other adapted method, such as histology, for example.

According to its structure, the material according to the invention has an adjustable absorbable character. Thus, according to the envisaged applications, it may be implanted for variable durations: a short-term implantation, translating as a total absorption of the material at the end of a maximum time period of 30 days, or a long-term implantation translating as a complete absorption of the material at the end of a time period longer than 30 days.

Generally, the present invention is advantageous in the medical field, said material being usable as a compress, implantable dressing, prosthesis, vascular endoprosthesis or recellularization matrix, for an organ implant or regeneration.

It advantageously is a compress. Conventionally, a compress may be in sponge or textile form. In the context of the invention, a compress preferably corresponds to a textile obtained by means of the claimed method.

More generally, the primary use of the solid material according to the invention depends on the type of material present:

the fibers or micro-fibrils may be associated in a nonwoven or a foam, hence the use of the material according to the invention for the forming of a nonwoven or of a foam;

the fibers or micro-fibrils may be associated in a yarn, hence the use of the material according to the invention to form a yarn;

a yarn may be woven or knit to form a fabric, hence the use of the material according to the invention to form a fabric;

a fabric may be used as a compress, hence the use of the material according to the invention as a compress;

the fibers or micro-fibrils may be divided to obtain a powder.

In the context of the invention, a method of obtaining a material having all the above-mentioned characteristics has been disclosed. More specifically, the invention aims at a method providing a solid material based on a polymer having its cellobiose units exhibiting the following characteristics:

at least some of the cellobiose units have at least one carboxylic acid function attached to the $C_6$ carbon, the other $C_6$ carbons having a primary alcohol function attached thereto; and at least some of the cellobiose units have at least one of the two rings open between the $C_2$ and $C_3$ carbons, the other $C_2$ and $C_3$ carbons forming a ring and having an alcohol function attached thereto.

According to the invention, this method comprises the steps of:

a first step of placing in contact a solid material based on polymer containing cellobiose units and an oxidizing mixture comprising a hypohalite, a halite, and an oxoammonium salt or a precursor of said salt; and then a second step of placing in contact the material thus processed and a solution of periodic acid or a salt thereof.

According to another aspect, the present invention aims at a method of processing a solid material based on polymer containing cellobiose units comprising the following steps:

a first step of placing in contact the solid material and an oxidizing mixture comprising a hypohalite, a halite, and an oxoammonium salt or a precursor of said salt; and then a second step of placing in contact the material thus processed and a solution of periodic acid or of a salt thereof.

According to a specific embodiment and in a third step, the material thus processed is placed in contact with a halite solution.

This method may be implemented either directly on the already shaped material, that is, a textile, either on yarns which will then be weaved or knit, or even on fibers which will then be associated by electrospinning or carding/interlocking in the form of nonwoven, oriented or not, or of yarns. Advantageously, the method according to the invention is implemented on a solid material having its final form advantageously in the form of a textile.

It can however be envisaged to change the form of the material between steps. Thus, and as an example, the first step may be implemented on fibers which may, between the 2 steps, be assembled in nonwoven or yarn form. Similarly, the first step may be carried out on yarns which will then be knit or woven, the second step being carried out on the knitted fabric or the woven fabric.

Advantageously, upstream of the method according to the invention, the material may be submitted to a finish removal step enabling to remove the fat used in spinning. This fat is essentially formed of yarning oils and of acrylate glue coating the filaments. Different finish removal protocols are known in prior art and may be implemented.

According to a specific embodiment, the solid material based on polymer comprising cellobiose units, submitted to the method according to the invention, comprises no oxidized cellulose.

"Comprising no oxidized cellulose" means, in the sense of the present invention, having a degree of oxidation smaller than 1%. This preferably relates to natural or synthetic cellulose fibers, or synthetic fibers or also natural fibers possibly containing cellulose, but comprising no oxidized cellulose, that is, having received no specific oxidizing processing.

Synthetic fibers means fibers which have no natural precursor polymer, such as fibers obtained by polymerizing of a synthetic monomer, for example, a petroleum product.

Synthetic fibers, absorbable or not, particularly comprise polyamides such as nylons, polyesters, polyacrylates, polyurethanes, polylactic and polyglycolic acids, polyethylene glycols, poly-α-olefins, and halogenated polymers, the copolymers or combinations thereof.

The first step of the method according to the invention thus is that enabling to selectively oxidize at least one primary alcohol group located in position 6 of the cellobiose units present in the solid material.

This first step is carried out in the presence of a hypohalite, of a halite, and of an oxoammonium salt or of a precursor of said salt, advantageously in aqueous solution.

In the context of the present invention, "oxoammonium salt precursor" designates a chemical species capable of generating an oxoammonium salt by reaction with one of the components of the oxidizing mixture, particularly by oxidation by one of the mixture components.

Oxoammonium salts are water-soluble oxidizers capable of selectively oxidizing primary alcohols, when the reaction takes place in appropriate pH and temperature conditions. Oxoammonium salts preferred according to the invention are di-tert-alkyl salts, particularly 1-oxo-2,2,6,6-tetramethylpiperidine-1-oxyde salts, commonly called TEMPO, and the derivatives thereof.

The oxoammonium salts, which catalyze this first partial oxidation step, are regenerated in situ by a secondary or auxiliary oxidizing system, in the case in point in the presence of a hypohalite, preferably sodium hypochlorite (NaClO). The latter is in turn regenerated in situ by the reaction of a halite, preferably sodium chlorite $NaClO_2$, after it has reacted with the aldehydes newly formed by oxidation of the primary alcohol in position 6.

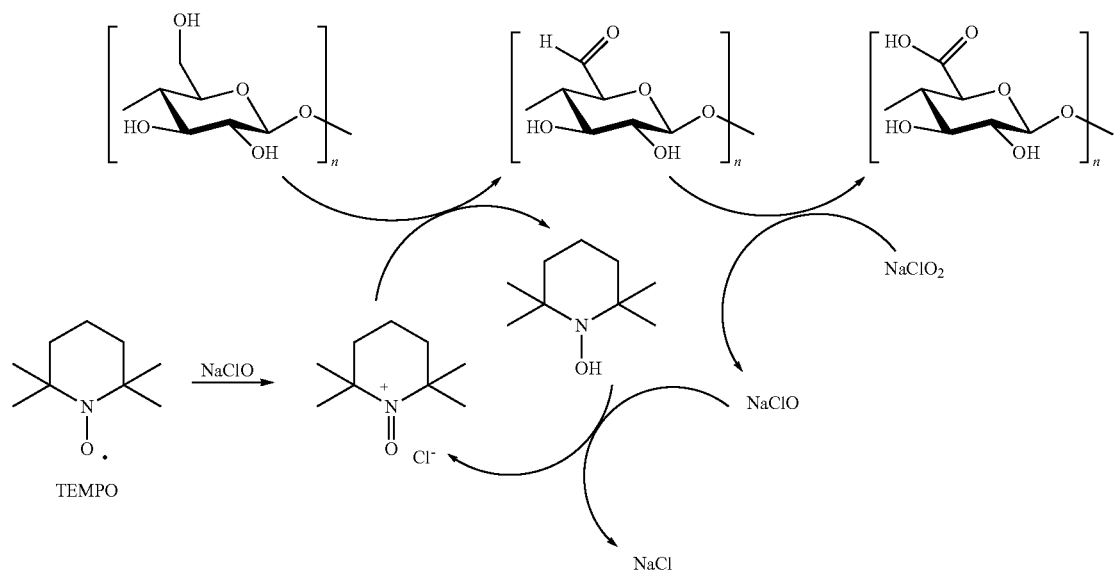

According to a preferred embodiment of the invention, the first oxidation step is carried out in the presence of a substoichiometric quantity of oxoammonium salt or of a precursor thereof with respect to the quantity of anhydroglucose units present in the processed material. In practice, and in adapted fashion, the oxoammonium salt or a precursor thereof amounts to from 0.0003 to 0.0006 mole per gram of polymer containing cellobiose units (cellulose).

It should be noted that the quantities of reactants mentioned in the description correspond to the specific case where the polymer containing cellobiose units is cellulose. Thus, in the case of a mixture of polymers or of polymers which do not only have cellobiose units, these quantities are calculated according to the number of cellobiose units present.

According to another preferred embodiment of the invention, the first oxidation step is carried out in the presence of a hypohalite quantity substoichiometric with respect to the quantity of anhydroglucose units present in the processed material, advantageously from 0.0006 to 0.0049 mole of hypohalite per gram of polymer containing cellobiose units (cellulose). Typically, a quantity of 0.0012 mole of hypohalite per gram of polymer containing cellobiose units (cellulose) is used.

According to another preferred embodiment of the invention, the first oxidation step is carried out in the presence of a stoichiometric excess of halite with respect to the quantity of anhydroglucose units present in the processed material, advantageously from 0.006 to 0.025 mole of halite per gram of polymer containing cellobiose units (cellulose). Typically, a quantity of 0.012 mole of halite per gram of polymer containing cellobiose units (cellulose) is used.

According to a specific embodiment, the 3 components are present in the oxidizing mixture since the beginning of the reaction.

Advantageously, the oxidizing mixture is formulated in demineralized water, to avoid altering the ionic force and the pH.

According to another aspect of the invention, the first oxidation step is advantageously carried out in a reaction medium having a neutral, or even slightly acid pH, advantageously in the range from 5 to 7. In other words, this reaction is carried out at a pH in the range from 5 to 7.

According to another aspect of the invention, this oxidation step is preferably carried out at a temperature greater than 40° C., advantageously in the order of 60° C.

Typically, this oxidation reaction takes place for a duration in the range from 1 to 6 hours, advantageously from 4 to 5 hours.

According to a specific embodiment, the material obtained at the end of this first step has an oxidation rate in the range from 10 to 16%, advantageously in the range from 12 to 15%.

A radical way to stop the oxidation reaction is to add to the reaction medium a primary alcohol, such as an excess of ethanol which will react with the oxoammonium salt and considerably dilute by mass effect the reaction with cellulose.

At the end of this first step, it may be useful to protonate the carboxylic acid functions present in the material thus processed.

Conventionally, this step is carried out by incubation of the material in a protonation medium. This is advantageously performed by incubation in hydrochloric acid (HCl), advantageously in one or a plurality of HCl baths from 0.1 to 1 mol/l (N), for a plurality of hours.

In practice, and to avoid manipulations of the processed material, the oxidation medium may be eliminated by discharge and replaced with the protonation medium.

At the end of this first step of oxidation and possibly of protonation, the material is advantageously washed and dried.

The compress is advantageously washed in a medium containing a solvent and/or water. An alcohol and/or demineralized water and/or acetone form a preferred washing medium, for example, ethanol at 50% and then ethanol at 95%.

Such washings may be repeated and generally last for a few hours, advantageously from 1 to 10 hours.

Appropriately, the material thus processed is dried by any adapted means, particularly with static or dynamic air or also in vacuum, and this, advantageously, for a plurality of hours.

The second oxidation step is carried out in the presence of periodic acid, or of a salt thereof, in the reaction medium. In other words, the material is incubated in a solution of periodic acid, or of a salt thereof. It advantageously is an aqueous solution.

The periodate ion is known to split glycols and turn them into dialdehydes. Thereby, the polymeric chain is not cut, but rather acquires a greater flexibility by opening of the rings. In the context of the invention, it has been shown that it is possible to modulate the absorption properties of the processed material by varying the intensity (time, temperature, reactant concentration, . . . ) of this step: the more the reaction is "boosted", the faster the obtained material is absorbed.

Advantageously, the periodic acid or a salt thereof is present by up to from 0.003 to 0.012 mole per gram of polymer containing cellobiose units (cellulose), advantageously 0.006 mole par gram de polymer containing cellobiose units (cellulose).

Advantageously, the periodic acid salt is sodium periodate.

According to another aspect of the invention, the second oxidation step is carried out at a pH in the range from 2 to 5, advantageously equal to 3.

According to another aspect of the invention, this second step is carried out at a temperature in the range from 5 to 60° C., advantageously equal to 35° C.

Further, the conventional duration of this step is advantageously in the range from 1 to 6 hours, advantageously equal to 3 h.

Advantageously, this reaction occurs away from light.

As already mentioned, a third oxidation step may be implemented on the solid cellulosic material having undergone the first two oxidation steps.

This third step is then carried out in the presence of a halite, advantageously in the presence of an aqueous halite solution. This step enables to selectively oxidize the aldehyde functions obtained after the reaction to periodate into carboxylic acid functions. Preferably, the halite is a chlorite, and more preferably sodium chlorite.

Advantageously, the solution comprises from 0.0025 to 0.012 mole of halite per gram of polymer containing cellobiose units (cellulose), advantageously 0.006 mole per gram of polymer containing cellobiose units (cellulose).

According to a preferred embodiment, the third step is carried out at a pH in the range from 5 to 7, advantageously equal to 5.8.

The temperature at which this reaction takes place is advantageously greater than 15° C., more advantageously still equal to 35° C. As a variation, it may be carried out at ambient temperature.

Typically, the third reaction of oxidation of the cellulosic material is carried out for a duration in the range from 0.25 to 2 hours, advantageously from 0.5 to 1 hour.

The conversion of the aldehyde functions into carboxylic acid functions enables, due to the measurement of the oxidation rate, to quantify the reaction occurring at the second step of the method according to the invention. Thus, and according to a preferred embodiment, the combination of steps 2 and 3 enables to increase the oxidation rate by from 1 to 7%, advantageously from 2 to 4%.

Thus, and according to the present invention, the oxidation of the cellobiose units occurs according to the following scheme:

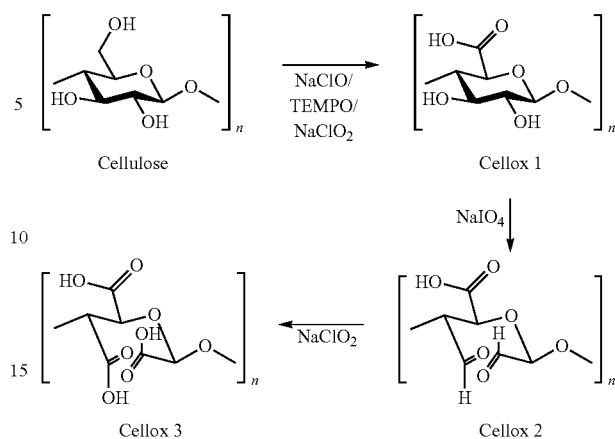

Advantageously, at the end of each of the steps of the method according to the invention, the material is washed in a bath of distilled water and/or of ethanol and/or of acetone, possibly repeatedly. It is then advantageously dried as described hereabove.

Finally, a possible acidification or protonation step, as described hereabove, may be implemented.

On the other hand and as known, a material based on oxidized cellulose should exhibit carboxylic acid functions, either protonated, or complexed with calcium ions ($Ca^{2+}$), to develop the desired haemostatic properties.

In the case where an oxidized material having carboxylic acid functions complexed with calcium ions ($Ca^{2+}$) is desired, there exist several possibilities:
- either the oxidation is performed by means of reactants in the form of calcium salts. In this case, at the end of the reaction, the carboxylic acid functions appear in $(COO)_2$ Ca form;
- as a variation, it may be envisaged to perform the incubation in the presence of the calcium source (particularly calcium acetate or $CaCl_2$), after the oxidation;
- a third possibility is to incubate the compress in a medium containing a calcium source, after the protonation step. Here again, particularly adapted calcium sources are calcium acetate or $CaCl_2$. In this new step, the $Ca^{2+}$ ions will replace the protons of the carboxylate functions.

At the end of the method according to the invention, the processed material is submitted to one or a plurality of washings, advantageously with ethanol, and to a drying, carried out in the above-described conditions.

It may also be submitted to treatments associated with the targeted application: individual packaging, sterilization, etc.

It should be noted that, as demonstrated in the context of the present application, the order of the first two steps of the method is crucial, particularly when implemented on a textile. Indeed, an inversion of the two steps causes a degradation of the textile.

The method according to the invention capable of being implemented on any solid material, and particularly on a textile, has many advantages, including the following:
- It involves inexpensive reactants, which are easy to handle and environmentally friendly, unlike $NO_2$.
- When it is implemented on a textile, it provides a product having mechanical resistance, haemostasis, and absorption characteristics compatible with a use as a compress.

It enables to accurately control the degree and the regioselectivity of the oxidation reactions. Thus, the first oxidation step provides a degree of oxidation greater than or equal to 10% or even greater than or equal to 12%; the second step, when it is followed by a conversion of the aldehyde functions into carboxylic acid, further enables to increase the oxidation level by at least 1%, or even 7%.

It enables to control oxidative modifications, while other techniques such as $NO_2$ are non-selective: the attacked alcohol functions as well as the groups formed are not controlled. As an example, $NO_2$ attacks the $C_6$ but also the $C_2$ and $C_3$, at the level of which it generates the forming of aldehyde as well as of carboxylic acid and ketone (with no opening of the ring in this last case), while leaving nitrogen traces on the final product.

EXAMPLES OF EMBODIMENT

The invention and the resulting advantages will better appear from the non-limiting embodiments discussed hereafter.

These examples are based on fabrics made from knitted yarns of regenerated cellulose (or viscose), in crochet or jersey stitch.

I/Method of Obtaining the Solid Cellulosic Material

1) First step:

This step enables to partially oxidize the cellulose via the conversion of primary alcohol functions attached to the $C_6$ carbon of the cellobiose units into carboxylic acid functions.

The general conditions of this step are described in Table 1 hereafter:

| | |
|---|---|
| TEMPO (mole per gram of cellulose) | from 0.0003 to 0.0006, for example 0.0006 |
| NaClO (mole per gram of cellulose) | from 0.0006 to 0.0049, for example 0.0012 |
| $NaClO_2$ (mole per gram of cellulose) | from 0.006 to 0.025, for example 0.012 |
| pH of the reaction medium | from 5 to 7, for example 5.8 |
| Temperature (° C.) | 60 |
| Duration of the reaction (h) | from 1 to 6, typically from 4 to 5 |

Under a ventilator, 200 ml of a sodium acetate buffer solution (0.5 M, pH=5.8) are placed in a 1-1 Erlenmeyer, after which 0.12 mole of $NaClO_2$ is added. 10 g of knitted regenerated cellulose are then placed in the $NaClO_2$ solution. 0.006 mole of TEMPO and an aqueous solution of NaClO with 2% of active chlorine (0.012 mol) are then added to the reaction mixture. The total volume of the reaction mixture is 500 ml. The Erlenmeyer is closed and placed in a thermostatic water bath maintained at a 60° C. temperature for a duration from 1 to 6 h, and typically from 4 to 5 h. The oxidation is stopped by addition of an excess of ethanol.

The partially oxidized cellulose fabric is wrung and then incubated for 12 h in an aqueous solution of N HCl on an orbital shaker. The aqueous solution of N HCl is renewed and the incubation is carried on for 2 h.

The partially oxidized cellulose fabric is wrung and then washed with 50% ethanol for 1h on an orbital shaker. This operation is repeated twice. The fabric is then wrung, and then washed with 95% ethanol for 1 h on an orbital shaker, and then finally wrung and air-dried under a ventilator for at least 12 h.

2) Second step:

This step enables to open the ring between the $C_2$ and $C_3$ carbons of the cellobiose units. Simultaneously, the alcohol functions attached to these carbons are oxidized into aldehyde functions.

The general conditions of this sten are disclosed in Table 2 hereafter:

| | |
|---|---|
| $NaIO_4$ (mole per gram of cellulose) | from 0.003 to 0.012, for example 0.006 |
| pH of the reaction medium | from 2 to 5, for example 3 |
| Temperature (° C.) | from 5 to 60, for example 35 |
| Duration of the reaction (h) | from 1 to 6, for example 3 |

10 g of the material obtained at the end of the first partial oxidation step are mixed with 0.06 mole of periodate ion in a 1-1 Erlenmeyer. The total volume of the reaction mixture is 500 ml. The pH is adjusted to 3 and the reaction is carried out under stirring for 3 h, at a 35° C. temperature and away from light. The cellulosic material is then rinsed twice with distilled water before being submitted to an acidification and to a washing with ethanol, as described hereabove.

3) Third step (optional):

This step enables to oxidize the aldehyde functions attached to the $C_2$ and $C_3$ carbons of the cellobiose units into carboxylic acid functions.

The general conditions of this sten are disclosed in Table 3 hereafter:

| | |
|---|---|
| NaClO2 (mole per gram of cellulose) | from 0.0025 to 0.012, for example 0.006 |
| pH of the reaction medium | from 5 to 7, for example 5.8 |
| Temperature (° C.) | greater than 15° C., for example, 35° C. |
| Duration of the reaction (h) | from 0.25 to 2, for example 1 |

10 g of the material obtained at the end of the first two steps are mixed with 0.06 mole of sodium chlorite prepared in an acetic buffer at pH 5.8. The reaction is carried out for 30 minutes, at ambient temperature. The total volume of the reaction mixture is approximately 150 ml. The cellulosic material is then rinsed twice with distilled water before being submitted to an acidification and to a washing with ethanol, as described hereabove. The material is then dried.

4) Monitoring of the forming of aldehyde functions:

The presence of aldehyde functions has been monitored by means of reactant Purpald® which reveals their presence by the appearing of an intense purple color.

The intensity of this coloring has been graded for different products: from 0 for a solution having no purple coloring to +++ for a very intense purple solution.

The results are disclosed in Table 4 hereafter:

| Tested product | Non-processed cellulose textile | Cellulose textile after the first step | Cellulose textile after the second step | Surgicel ® |
|---|---|---|---|---|
| Intensity of the purple coloring | 0 | 0 | + + + | + + |

These experiments show that the first step generates no aldehyde function at the $C_6$ level, while the second step causes at the same time the opening of the ring between the $C_2$ and $C_3$ carbons and the generation of aldehyde functions at the level of these carbons. This test is also positive on a Surgicel® compress obtained by a $NO_2$ processing.

II/Evaluation of the Physical Properties of the Material

1) Degree of oxidation of the obtained fabric:

The degree of oxidation of the partially oxidized cellulose fabric represents the mass of carboxylic acid groups contained in 100 g of said fabric. This value is measured by titrimetry, according to the calcium exchange method described by Sobue and Okubo, and recommended by the United States Pharmacopeia (USP, 1990).

The degree of oxidation of different fabrics (test 1: crochet; test 2: jersey), obtained by means of the method in two steps (TEMPO/NaClO/NaClO$_2$ followed by NaIO$_4$), has been measured.

The experimental conditions and the measured degrees of oxidation are disclosed in Table 5 hereafter:

| Step | Nature of the cellulose fabric | Test 1 crochet | Test 2 Jersey |
|---|---|---|---|
| 1 | TEMPO (mol/g of cellulose) | 0.0006 | 0.0006 |
|  | NaClO (mol/g of cellulose) | 0.0012 | 0.0012 |
|  | NaClO$_2$ (mol/g of cellulose) | 0.012 | 0.012 |
|  | Temperature (° C.) | 60 | 60 |
|  | Duration of the reaction (h) | 6 | 6 |
| 2 | NaIO$_4$ (mol/g of cellulose) | 0.006 | 0.006 |
|  | Temperature (° C.) | 35 | 35 |
|  | Duration of the reaction (h) | 3 | 3 |
| Degree of product oxidation (%) |  | 13.44 | 13.55 |

As a conclusion, the oxidation rate is sufficient for the material obtained by means of the method according to the invention to have good haemostatic properties.

2) Stability of the obtained fabric:

The obtained partially oxidized cellulose fabric keeps an excellent mechanical resistance after 1 month, in a stove at 60° C.

This sample keeps a fine aspect, with no degradation. This same sample has been sterilized by irradiation with β rays, and has then been submitted to an aging process which has caused no degradation of the fabric.

A stability equivalent to that of the Surgicel® product has also been observed after 3 month at 25° C. and in controlled humidity, or after a 60° C. thermal stress.

3) Apparent degree of polymerization of the obtained fabric:

The apparent degree of polymerization has been measured by the viscosity measurement according to standard NF G06-037 (December 1981).

The obtained results are disclosed in Table 6 hereafter:

| Product | Degree of polymerization |
|---|---|
| Non-processed cellulose | 270 |
| Surgicel ® (reference product) | 20 |
| Crochet (Test 1) | 20 |
| Jersey (Test 2) | 20 |

As a conclusion, the method according to the present invention results in a material (tests 1 and 2) with an apparent polymerization degree, measured by the viscosity, of the same order as the reference product (Surgicel®).

III/Evaluation of the Preclinical Properties of the Material

1) Absorption:

The preclinical studies have been carried out by means of 3 types of implants according to standard ISO10993-6 (2007):

Surgicel®, taken as a reference;
implant Test1 corresponds to a jersey-type material, processed according to the first oxidation reaction (NaClO, TEMPO, and NaClO$_2$) for 6 hours, and then according to the second periodate oxidation reaction for 6 hours;
implant Test2 has been submitted to a processing equivalent to that of Test1, except for the duration of the second periodate oxidation reaction, of 3 hours only.

These studies have been carried out on 6 female rats of the Sprague-Dawley strain. The incision areas have been shaved, the rats have been anaesthetized. 2 incisions on each side of the spine have been made (one so-called cranial incision and one so-called caudal incision). 4 implants of 1×1 cm have been placed per animal. The cutaneous incisions have been closed with clips.

After 14 days, the rats have been sacrificed by inhalation of $CO_2$. The products have been taken off and the implantation sites have been removed and macroscopically analyzed.

The presence of a necrosis, of an exudate, of a neovascularization, and of an encapsulation have been evaluated at the implantation site, by means of a scoring chart. The rating scale is the following: absent (0); light reaction (1); moderate reaction (2); strong reaction (3); severe reaction (4).

For the absorption, the residual persistence of the product is evaluated. The scale is the following:
grade (0) is given in case of a total degradation;
grade (1) is given if there remain small fragments of the product;
grade (2) is given in case of a moderate persistence;
grade (3) is given when the product is intact.

The results are disclosed in Table 7 hereafter:

|  | Average of the scores (n = 3 rats, 4 implantation sites for each product*) | | |
|---|---|---|---|
| Condition | Test1 (periodate = 6 h) | Test2 (periodate = 3 h) | Reference (Surgicel ®) |
| necrosis | 0 | 0 | 0 |
| exudate | 0 | 0 | 0.25 |
| neovascularization | 0.5 | 0.5 | 0.5 |
| encapsulation | 0 | 0 | 0 |
| absorption | 0.25 | 1 | 0.67 |

*only three implantation sites have been evaluated for the reference product (Surgicel ®).

At J14, a light to moderate reaction of the test products and of the control compress can be observed (exudate and neovascularization). The test products are mainly absorbed; for product Test1, 3 sites are totally absorbed out of 4 and 1 site has small fragments; for product Test2, 3 sites are not absorbed; finally, for the control product, 2 sites out of three are absorbed and 1 site exhibits a moderate persistence.

Thus, the material obtained by the method according to the invention has a absorption speed comparable to reference commercial product Surgicel®, and even better, if it is considered that the fabric used in this study has a grammage greater than that of Surgicel®.

Further, these studies show that the longer duration of the periodate oxidation reaction, the faster the absorption. Thus, the control of the duration of the second step of the method according to the invention enables to modulate the absorption speed of the cellulosic material, according to the applications for which it is intended.

2) Haemostasis:

The haemostatic performance has been tested on the processed cellulosic textile on animals on a per-operative bleeding model versus reference product Surgicel®. The methodology comprises creating, on pigs, lesions of square shape and of predetermined surface area on organs (spleen and liver) and then to cover the wounds thus created with the compresses to be tested.

The observations bear on the behavior in contact with blood and the time necessary to establish the haemostasis (see Table 8 hereafter). The spleen and liver have been selected as test organs since both the nature of their tissue and the intensity of the bleeding that they generate are different.

| Organ | Haemostasis time | |
|---|---|---|
| | Processed cellulose textile | Surgicel ® |
| spleen | 9 minutes | 10 minutes |
| liver | 2 min 45' | 3 min |

A haemostatic behavior of the tested cellulosic textile comparable to that of the reference product can be observed, whatever the tested organ: the behavior in contact with blood is identical to that of the reference and the time necessary to obtain the stopping of the bleeding is equivalent for each considered organ.

This study enables to highlight the haemostatic power of the material.

IV/Characteristics of the Product Obtained by Inversion of Steps 1 and 2:

The general conditions are listed in Table 9 hereafter:

| | |
|---|---|
| NaIO$_4$ (mole per gram of cellulose) | 0.006 |
| pH of the reaction medium | 3.0 |
| Temperature (° C.) | 35° C. |
| Duration of the reaction | 3 h |

Step 1:

10 g of cellulose are mixed with 0.06 mole of periodate ion in a 1-1 Erlenmeyer. The total volume of the reaction mixture is 505 ml. The pH is adjusted to 3.0 and the reaction is carried out in a water bath under discontinuous stirring for 3 h, at a 35° C. temperature and away from light. The obtained cellulosic material is then rinsed twice with purified water before undergoing an acidification and then washed several times with ethanol. After being wrung, the material is dried for 16 h under an air flow.

Step 2:

The previous material, obtained in the dry state, is submitted to reaction TEMPO/NaClO/NaClO$_2$. The general conditions are listed in Table 10 hereafter:

| | |
|---|---|
| TEMPO (mole per gram of cellulose) | 0.0006 |
| NaClO (mole per gram of cellulose) | 0.0012 |
| NaClO$_2$ (mole per gram of cellulose) | 0.012 |
| pH of the reaction medium | 5.8 |
| Temperature (° C.) | 60 |
| Duration of the reaction | 5 h |

Under a ventilator, 200 ml of a buffer solution tampon of sodium acetate (0.5 M, pH=5.8) are placed in a 1-1 Erlenmeyer, after which 0.12 mole of NaClO$_2$ are added. 10.1 g of the previously obtained material are then placed in the NaClO$_2$ solution. 0.006 mole of TEMPO and an aqueous solution of NaClO with 2% of active chlorine (0.012 mol) are then added to the reaction mixture. The reaction volume is adjusted to 500 ml with sodium acetate buffer solution. The Erlenmeyer is closed and placed in a thermostatic water bath at 60° C. for 5 h.

At the end of the reaction, the textile has disappeared from the reaction medium. The reaction medium is then precipitated in the presence of ethanol but the obtained precipitate is inexploitable.

REFERENCES

Fujisawa S, Okita Y, Fukuzumi H, Saito T, Isogai A. 2011. Preparation and characterization of TEMPO-oxidized cellulose nanofibril films with free carboxyl groups. Carbohydrate Polymers 84(1):579-583.

Kumar V, Yang T. 1999. Analysis of carboxyl content in oxidized celluloses by solid-state 13C CP/MAS NMR spectroscopy. Int J Pharm. July 20;184(2):219-26.

Singh M, Ray A R, Vasudevan P, Verma K, Guha S K. 1979. Potential biosoluble carriers: biocompatibility and biodegradability of oxidized cellulose. Biomater Med Devices Artif Organs, 7(4):495-512.

Sobue H, Okubo M. 1956. Determination of carboxyl group in cellulosic materials with the "dynamic ion exchange method". Tappi, 39(6) :415.

The invention claimed is:

1. A method of obtaining a solid material based on a polymer comprising cellobiose units, wherein:
at least some of the cellobiose units have at least one carboxylic acid function attached to the $C_6$ carbon, the other $C_6$ carbons having a primary alcohol function attached thereto; and
at least some of the cellobiose units have at least one of the two rings open between the $C_2$ and $C_3$ carbons, the other $C_2$ and $C_3$ carbons forming a ring and having an alcohol function attached thereto, said method comprising the following steps:
a first step of placing in contact a solid material based on polymer containing cellobiose units and an oxidizing mixture comprising a hypohalite, a halite, and an oxoammonium salt or a precursor of said salt, wherein the first step is carried out at neutral or acidic pH, and wherein the solid material comprises an assembly of yarns or fibers that form a unitary entity that is insoluble in water at said pH; and
then
a second step of placing in contact the material comprising the assembly of yarns or fibers that form a unitary entity thus processed and a solution of periodic acid or of a salt thereof,
wherein the solid material so obtained has a degree of oxidation which corresponds to the conversion of alcohol and/or aldehyde functions in the cellobiose units into carboxylic acid functions, of greater than 10% calculated by the mass of said carboxylic acid functions contained in 100 g of the solid material.

2. The method according to claim 1, wherein said method comprises a third step of placing in contact the material having been submitted to the first two steps and a halite solution.

3. The method according to claim 2, wherein the halite solution comprises from 0.0025 to 0.012 mole of halite per gram of polymer.

4. The method according to claim 2, wherein the third step is carried out at a pH in the range from 5 to 7.

5. The method according to claim 2, wherein the third step is carried out at a temperature greater than 15° C.

6. The method according to claim 2, wherein the third step is carried out for a duration in the range from 0.25 to 2 hours.

7. The method according to claim 1, wherein the oxidizing mixture comprises from 0.0003 to 0.0006 mole of oxoammonium salt or a precursor of said salt, per gram of polymer.

8. The method according to claim 1, wherein the oxidizing mixture comprises from 0.0006 to 0.0049 mole of hypohalite per gram of polymer.

9. The method according to claim 1, wherein the oxidizing mixture comprises from 0.006 to 0.025 mole of halite per gram of polymer.

10. The method according to claim 1, wherein the first step is carried out at a pH in the range from 5 to 7.

11. The method according to claim 1, wherein the first step is carried out at a temperature greater than 40° C.

12. The method according to claim 1, wherein the first step is carried out for a duration in the range from 1 to 6 hours.

13. The method according to claim 1, wherein the solution of periodic acid or of a salt thereof comprises from 0.003 to 0.012 mole of periodic acid, or of a salt thereof, per gram of polymer.

14. The method according to claim 1, wherein the second step is carried out at a pH in the range from 2 to 5.

15. The method according to claim 1, wherein the second step is carried out at a temperature in the range from 5 to 60° C.

16. The method according to claim 1, wherein the second step is carried out for a duration in the range from 1 to 6 hours.

17. The method according to claim 1, wherein the first step is stopped by addition of an excess quantity of primary alcohol.

18. The method according to claim 1, said method optionally comprising a third step of placing in contact the material having been submitted to the first two steps and a halite solution, wherein between the first two steps and/or after the second step and/or after the third step, the material is incubated in a protonation medium.

19. The method according to claim 18, wherein after the material is incubated in the protonation medium, the material is submitted to washing and optionally drying.

20. The method according to claim 1, wherein the oxidizing mixture comprises:
   from 0.0003 to 0.0006 mole of TEMPO per gram of polymer;
   from 0.0006 to 0.0049 mole of sodium hypochlorite per gram of polymer; and
   from 0.006 to 0.025 mole of sodium chlorite per gram of polymer.

21. The method according to claim 1, wherein the first step generates no aldehyde functions at the $C_6$ carbon of the cellobiose units.

* * * * *